United States Patent
Beguin et al.

(10) Patent No.: US 7,445,638 B2
(45) Date of Patent: Nov. 4, 2008

(54) HUMERAL IMPLANT FOR SHOULDER PROSTHESIS

(75) Inventors: Laurent Beguin, 14 Chemin Persles, F-69540 Irigny (FR); Denis Bouttens, 21 Route de Merlimont - Hameau de la Capelle, F-62170 Saint Josse (FR); Charles Cohn, le Mas Tou - le Logis de Paris, F-83600 les Adrets de l'Esterel (FR); Geert Declercq, de Dreef Van Zonnebos 13, B-2970 Schilde (BE); Yann Brunnarius, Saint Peray (FR); Jean Grimberg, 8 Rue des Platanes, 78150 Le Chesnay (FR); Dominique Huguet, 8 Rue des Chênes, F-44700 Orvault (FR); Eric Lesprit, 24 Rue de Lyon, 33000 Bordeaux (FR); Pierre Massart, 20 Allé Graziella, F-73100 Tresserve (FR); Bruno Rio, 53 Rue du Grand Verger, 54000 Nancy (FR); Jacques Teissier, 336 Chemin de la Rocheuse, F-34170 Castelnau le Lez (FR); Bruno Toussaint, 22 Rue de la Barallaz, F-74940 Annecy le Vieux (FR); Bruno Zipoli, 36 Impasse des Coquelicots, F-40150 Hossegor (FR)

(73) Assignees: Biomet France, Valence (FR); Laurent Beguin, Irigny (FR); Denis Bouttens, Saint Josse (FR); Jean Grimberg, le Chesnay (FR); Jacques Teissier, Castelnau Le Lez (FR); Dominique Huguet, Orvault (FR); Bruno Toussaint, Annecy le Vieux (FR); Eric Lesprit, Bordeaux (FR); Bruno Zipoli, Hossegor (FR); Charles Cohn, les Adrets de l'Esterel (FR); Pierre Massart, Tresserve (FR); Geert Declercq, Schilde (BE); Bruno Rio, Nancy (FR)

( * ) Notice: Subject to any disclaimer, the term of this patent is extended or adjusted under 35 U.S.C. 154(b) by 0 days.

(21) Appl. No.: 11/071,540

(22) Filed: Mar. 3, 2005

(65) Prior Publication Data

US 2006/0200249 A1  Sep. 7, 2006

(51) Int. Cl.
*A61F 2/40* (2006.01)
*A61F 2/30* (2006.01)
(52) U.S. Cl. ............... 623/19.14; 623/19.12; 623/19.13
(58) Field of Classification Search ... 623/19.11–19.14, 623/21.13–23.44, 20.21–20.36
See application file for complete search history.

(56) References Cited

U.S. PATENT DOCUMENTS 3,694,820 A * 10/1972 Scales et al. ............. 623/19.12
3,728,742 A * 4/1973 Averill et al. ............. 623/20.21

(Continued)

FOREIGN PATENT DOCUMENTS

CH    WO 02/39933 A1    3/2002

(Continued)

*Primary Examiner*—David Isabella
*Assistant Examiner*—Ann Schillinger
(74) *Attorney, Agent, or Firm*—Burr & Brown (57) ABSTRACT

This adaptable humeral implant comprises an anchoring stem (1, 8) and a male insert (6) or a female insert (30, 31) which are able to cooperate with the glenoid cavity or a glenoid implant. It additionally comprises a removable support (5) intended to fit directly or indirectly to the upper end (3) of the anchoring stem (1, 8) and to cooperate with an intermediate neck (7), which is itself provided with means for cooperation with the male or female implant.

8 Claims, 7 Drawing Sheets

U.S. PATENT DOCUMENTS

| | | | | |
|---|---|---|---|---|
| 4,045,825 A | * | 9/1977 | Stroot | 623/19.14 |
| 4,662,891 A | * | 5/1987 | Noiles | 623/22.31 |
| 4,834,759 A | * | 5/1989 | Spotorno et al. | 623/22.3 |
| 4,865,605 A | * | 9/1989 | Dines et al. | 623/19.14 |
| 4,883,491 A | * | 11/1989 | Mallory et al. | 623/22.31 |
| 4,919,670 A | * | 4/1990 | Dale et al. | 623/19.14 |
| 5,314,479 A | * | 5/1994 | Rockwood et al. | 623/19.14 |
| 5,358,526 A | * | 10/1994 | Tornier | 623/19.14 |
| 5,489,309 A | * | 2/1996 | Lackey et al. | 623/19.14 |
| 5,507,819 A | * | 4/1996 | Wolf | 623/19.11 |
| 5,658,340 A | * | 8/1997 | Muller et al. | 623/19.14 |
| 5,702,486 A | * | 12/1997 | Craig et al. | 623/19.14 |
| 5,725,592 A | | 3/1998 | White et al. | |
| 5,910,171 A | * | 6/1999 | Kummer et al. | 623/18.11 |
| 5,944,758 A | * | 8/1999 | Mansat et al. | 623/19.14 |
| 5,972,032 A | * | 10/1999 | Lopez et al. | 623/22.32 |
| 6,171,340 B1 | * | 1/2001 | McDowell | 623/18.11 |
| 6,197,063 B1 | * | 3/2001 | Dews | 623/19.14 |
| 6,454,809 B1 | * | 9/2002 | Tornier | 623/22.32 |
| 6,520,994 B2 | * | 2/2003 | Nogarin | 623/19.14 |
| 6,524,342 B1 | * | 2/2003 | Muhlhausler et al. | 623/19.14 |
| 6,537,321 B1 | * | 3/2003 | Horber | 623/22.22 |
| 6,589,282 B2 | * | 7/2003 | Pearl | 623/19.14 |
| 6,620,197 B2 | * | 9/2003 | Maroney et al. | 623/19.14 |
| 6,676,705 B1 | * | 1/2004 | Wolf | 623/19.14 |
| 6,719,799 B1 | * | 4/2004 | Kropf | 623/19.14 |
| 6,736,851 B2 | * | 5/2004 | Maroney et al. | 623/19.12 |
| 6,736,852 B2 | * | 5/2004 | Callaway et al. | 623/19.14 |
| 6,942,699 B2 | * | 9/2005 | Stone et al. | 623/19.14 |
| 6,953,478 B2 | * | 10/2005 | Bouttens et al. | 623/19.11 |
| 7,011,686 B2 | * | 3/2006 | Ball et al. | 623/19.14 |
| 2004/0015238 A1 | * | 1/2004 | Buehler et al. | 623/22.12 |

FOREIGN PATENT DOCUMENTS

| | | |
|---|---|---|
| FR | 2 652 498 A1 | 4/1991 |
| FR | 2 674 122 A1 | 9/1992 |
| JP | 2005-103258 A * | 4/2005 |

* cited by examiner

HUMERAL IMPLANT FOR SHOULDER PROSTHESIS

The invention concerns the field of orthopaedic implants, in particular the field of shoulder prostheses. Generally, this type of prosthesis can take different forms. When the glenoid cavity is intact, which is especially the case in the event of a comminuted fracture, the shoulder prosthesis comprises a humeral element fixed in the medullary canal of the humerus and provided with a male implant of spherical shape intended to cooperate directly with the glenoid cavity. In the description below, this kind of device is referred to as a "humeral implant". In the case of destruction of the glenoid cavity, the prosthesis is in the form of a support implanted in the glenoid cavity and provided with a male or female insert for cooperating with a corresponding shape arranged in the humeral element.

The invention concerns more specifically a humeral implant which is adaptable in the sense that it is designed to receive either a male insert or a female insert, depending on the situation encountered in the articulation of the shoulder in question. In the description which follows, the expression "male insert" designates a prosthetic humeral head, in practice a sphere or hemisphere, intended to cooperate with the glenoid cavity, either directly or by way of a support provided with a corresponding female shape, in practice a cup. Likewise, the expression "female insert" designates a female part, in practice a cup intended to cooperate with a male part, in practice a sphere or hemisphere, and arranged on a support which is itself implanted in the glenoid region.

Document FR-A-2 652 498 describes a humeral implant of the same type comprising an anchoring stem, continued in its upper part by a head which has a recess designed to receive, by way of addition, either a male insert or a female insert. One of the disadvantages of this stem is that, in view of the size of the head of said stem, it is necessary to perform considerable resection of the spongy bone. In addition, the placement of the stem leads to a modification of the original position of the humeral head and thus its centre of rotation, which risks leading to a fracture of the metaphyseal zone of the humerus.

The object of the invention is therefore to make available an adaptable humeral implant which does not have the aforementioned disadvantages, particularly in terms of resection and of anatomy.

Consequently, the subject of the invention is an adaptable humeral implant comprising an anchoring stem and a male insert or a female insert which are able to cooperate with the glenoid cavity or a glenoid implant. This implant is characterized in that it additionally comprises a removable support intended to fit directly or indirectly to the upper end of the anchoring stem and to cooperate with an intermediate neck, which is itself provided with means for cooperation with the male or female implant.

In other words, the invention consists in having replaced the cone at the top of the humeral stem, described in document FR-A-2 652 498, with a removable support forming a basket designed to cooperate with the stem by way of a neck and to receive either a male insert or a female insert.

To avoid possible displacements of the various elements relative to one another once the prosthesis has been implanted, the male insert or female insert, and also the upper end of the stem, have means for cooperation with one another.

In practice, the support or basket is in the form of a circular seat provided with a through-opening and with at least three identical branches, preferably four identical branches substantially in the form of an arc of a circle which are spaced apart at intervals and give said support a general hemispherical shape. This hemispherical shape is in fact made necessary by the fact that, as will be seen below, the male insert and the female insert, also of hemispherical shape, cooperate closely with the support. Generally speaking, any means giving the support a general hemispherical shape may be envisaged, bearing in mind that the hemisphere cooperates with the upper end of the anchoring stem via its pole and by way of the neck and is anchored intimately and with interpenetration in the spongy bone of the humerus.

To permit positioning of the support or basket at the upper end of the stem, said upper end has a succession of notches or cuts spaced apart at intervals and intended to cooperate with the seat of the corresponding branches of the support.

The support or basket is fixed to the stem by means of the aforementioned neck. To avoid any displacement of the support relative to the stem once the prosthesis has been implanted, the anchoring stem has, again at its upper end, a recess of cylindrical or conical shape which is able to cooperate with said neck. In practice, this recess has a diameter slightly smaller than that of the seat of the support, so as to permit its adjustment in the stem.

In an advantageous embodiment, the recess of cylindrical shape is provided with an internal thread which is able to cooperate with a threading formed in the lower zone of the neck.

According to another characteristic, the stem has a cylindrical cross section whose diameter is almost constant. The diameter is in fact slightly greater at the upper end compared to the rest of the stem, the cross section at this level being elliptic with biconical widening.

In an advantageous embodiment, the stem has grooves in its distal zone, these making it possible to increase the contact surfaces with the cement or with the bone, and, consequently, to reinforce its secondary anchoring in the humeral shaft.

As has already been stated, the humeral implant according to the invention is of the adaptable type in the sense that it can receive a male insert, that is to say a prosthetic humeral head, or a female insert, that is to say a cup.

When the implant receives a male insert, said insert is in the form of a hemisphere whose base is provided with a conical recess able to cooperate with the upper end of the aforementioned neck. The other end of the neck passes through the seat of the support or basket so as to fit into or be screwed into the upper recess of the stem.

When the insert is a female insert, said insert is in the form of a cup which is continued by a central shaft positioned at its pole and functioning as the aforementioned neck and intended to cooperate with the upper recess of the stem. In practice, the diameter of the cup is chosen so that it fits into the support or basket of hemispherical shape.

The invention and the advantages which derive threrefrom will be clearer from the following illustrative embodiments which are given as indicative and non-limiting examples and with reference to the attached figures.

According to the invention, the humeral implant consists of three separate elements, namely an anchoring stem (1) or (8), a support (5) and a male insert or female insert.

Figure 1:
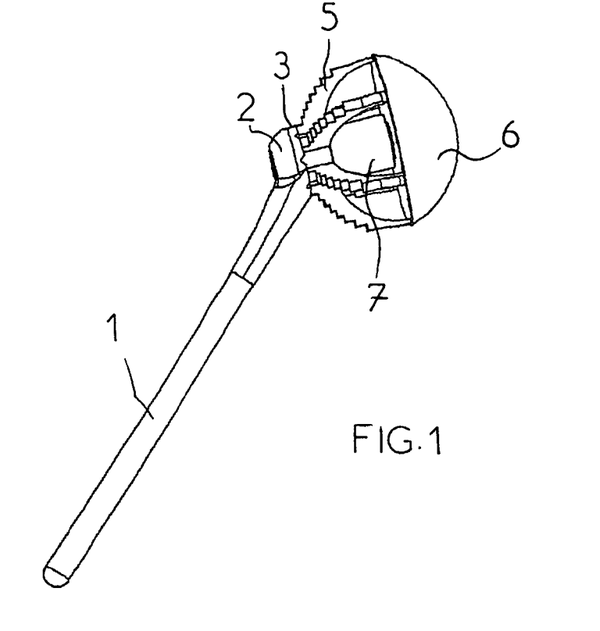
FIGS. 1 and 2 are diagrammatic representations of the humeral implant according to the invention provided with a prosthetic humeral head, in a side view and in an exploded view, respectively.
Figure 2:
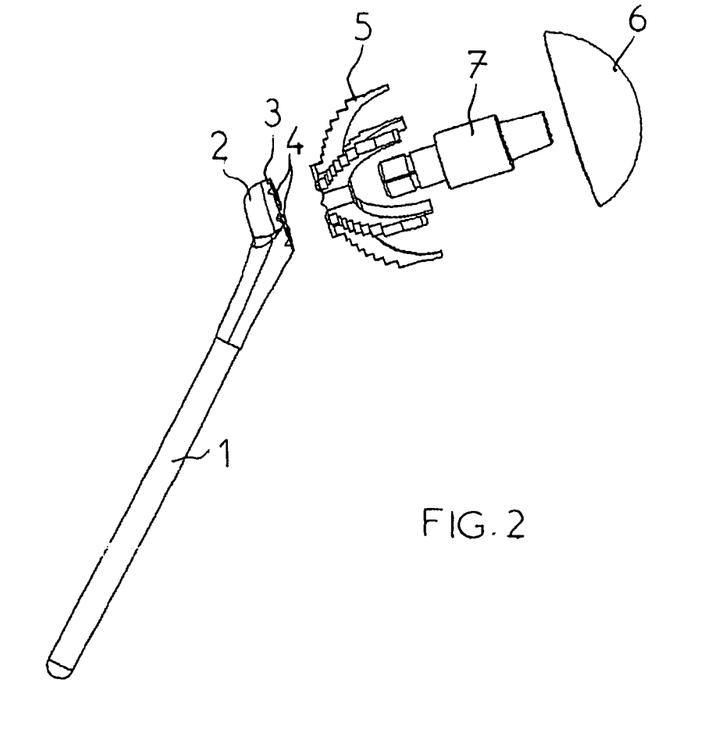
Figure 3:
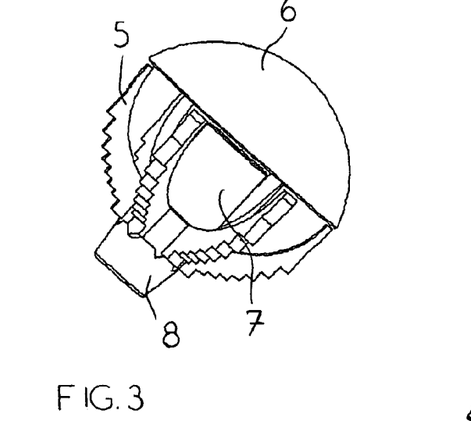
FIGS. 3 and 4 are more detailed diagrammatic representations of the upper part of the implant from FIGS. 1 and 2, and according to an alternative embodiment of the invention.
Figure 4:
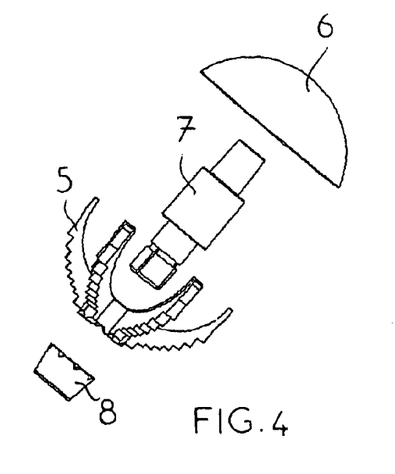
Figure 5:
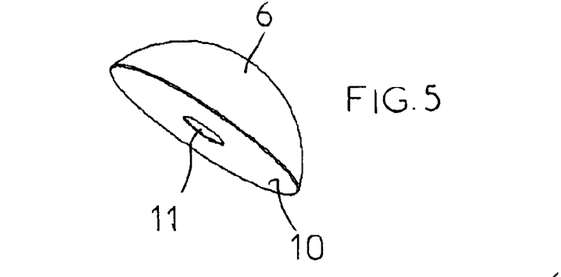
FIGS. 5 to 7 are diagrammatic representations of the prosthetic humeral head according to the invention, in perspective view and seen from below, respectively.
Figure 22:
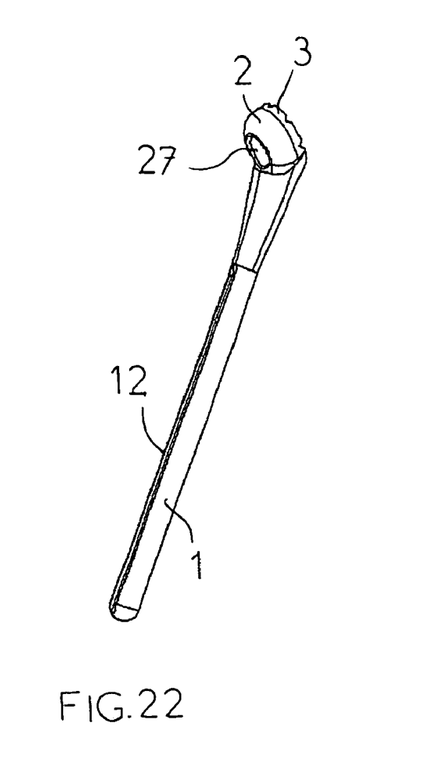
FIGS. 22 and 23 are diagrammatic perspective representations of the stem according to the invention, in two different views.
Figure 23:
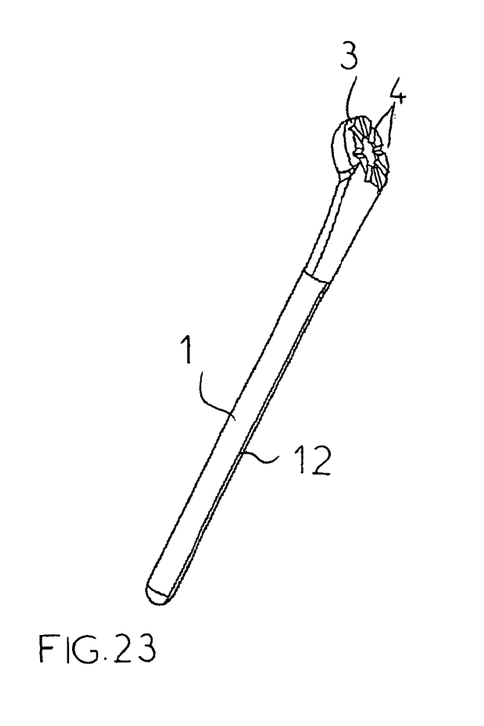

As is shown in FIGS. 1 and 2, and also in FIGS. 22 and 23, the anchoring stem (1) has a general cylindrical shape with almost constant cross section. However, its diameter is slightly greater at the upper end compared to the rest of the stem, the cross section at this area being elliptic with a biconical widening.

In addition, its distal part has grooves (12) able to optimize its secondary anchoring in the humeral bone.

According to the invention, the stem (1) is intended to receive a support in the shape of a basket (5), which is itself intended to receive a male or female insert.

Figure 18:
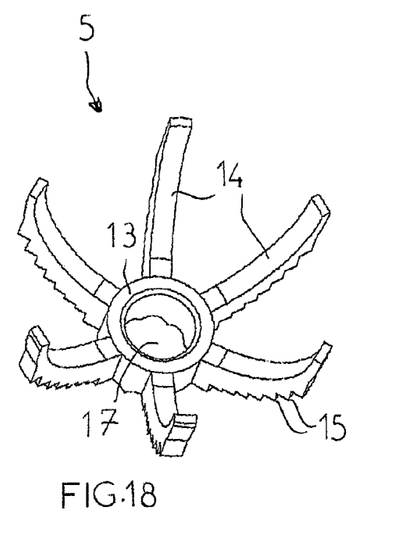
FIGS. 18 and 19 are diagrammatic perspective representations of the support or basket according to the invention.
Figure 19:
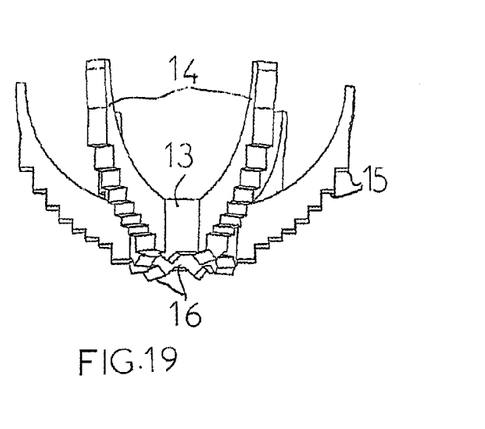

This basket (5), which can be seen better in FIGS. 18 and 19, consists of a cylindrical seat (13) from which there extend a plurality of branches (14) which are identical and spaced apart from one another at intervals. These branches in the general shape of an arc of a circle define a substantially hemispherical envelope. The outer face of the branches is provided with teeth intended to promote anchoring of said support in the spongy bone of the humerus. In addition, the cylindrical seat (13) is first provided with an aperture (17) intended to permit passage of a neck (7), described in more detail below, and additionally has, on its lower surface, radial sets of teeth (16) which are spaced apart at intervals and are intended to permit correct positioning of the basket (5) on the upper end (3) of the anchoring stem (1) or on the upper face (18) of an intermediate element or short stem (8), described with reference to FIGS. 20 and 21.

Figure 20:
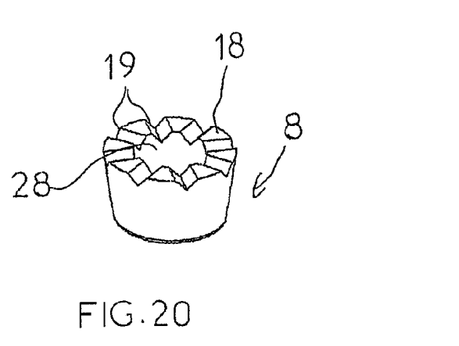
FIGS. 20 and 21 are diagrammatic perspective representations of an additional element which can be used in the context of the present invention.
Figure 21:
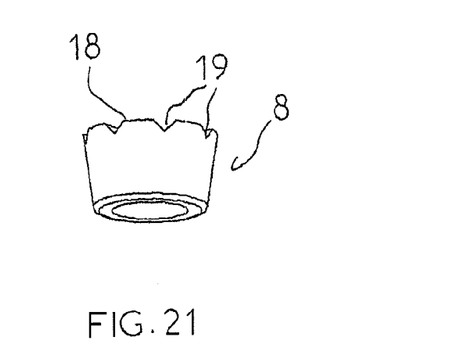

In fact, both the upper face (18) of the intermediate element (8) and the upper end (3) of the stem are provided with ribs (19, 4) of corresponding shape and pitch able to cooperate with these radial sets of teeth (16).

Figure 6:
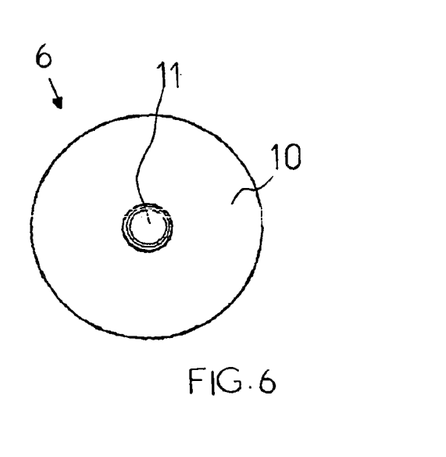
Figure 7:
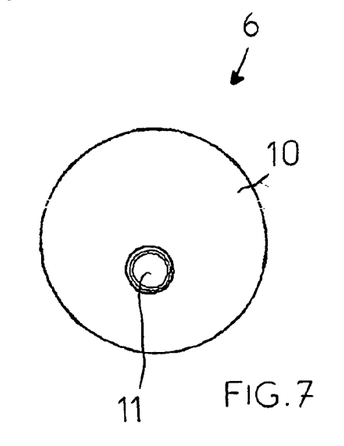
Figure 8:
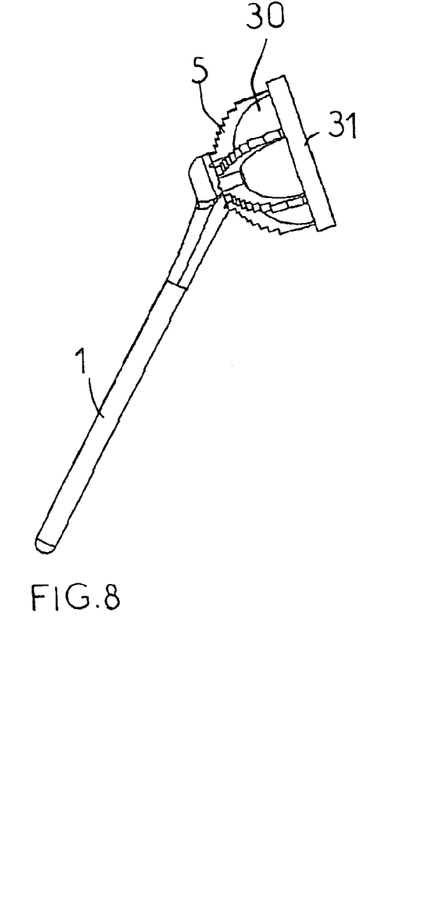
FIGS. 8 and 9 are diagrammatic representations of the humeral implant according to the invention, provided with a cup, in other words with a female insert, in a side view and an exploded view, respectively.
Figure 9:
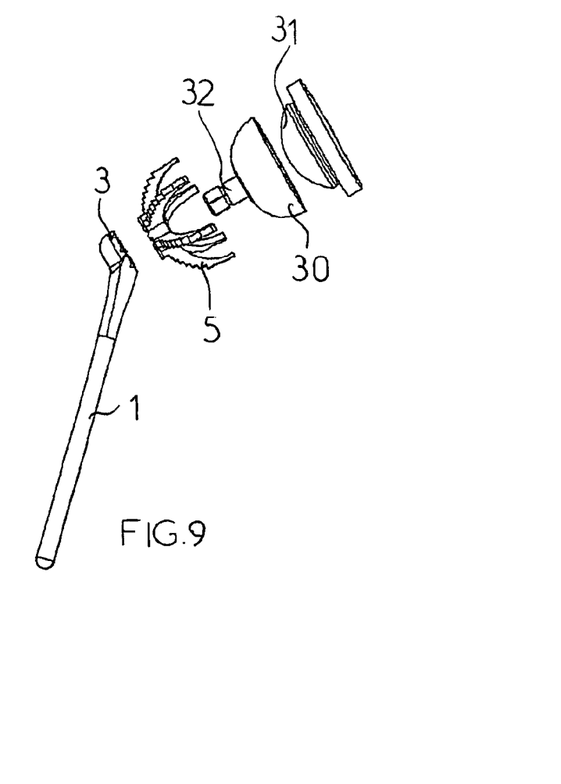
Figure 10:
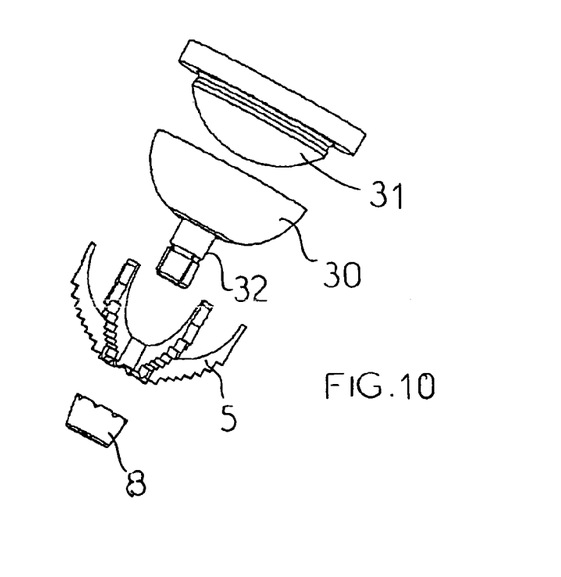
FIG. 10 is a more detailed diagrammatic representation and exploded view of a variant of the embodiment in FIGS. 8 and 9.
Figure 11:
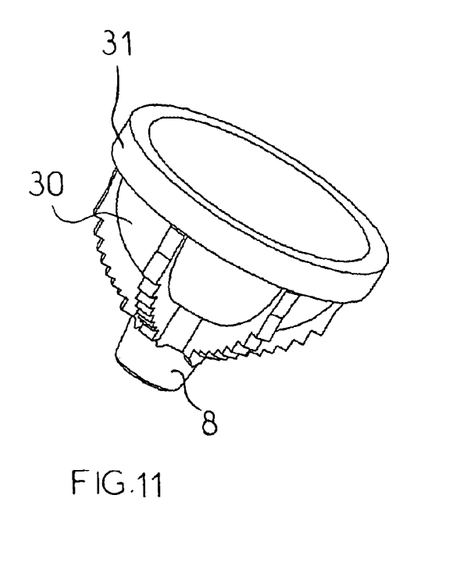
FIG. 11 is a diagrammatic perspective view of the support or basket according to the invention provided with a cup.

The male insert or prosthetic humeral head (6) consists of a substantially hemispherical cap, in particular made of stainless steel, chromium/cobalt alloy, or of any other material. The base (10) of this cap is provided with an aperture (11) centred (FIG. 6) or eccentric (FIG. 7) depending on the orientation sought by the practitioner. This aperture is intended to receive the upper end (20) of the neck (7). This is in the form of a morse cone which is able to fit in the aperture (10) of corresponding shape. It will be observed that said upper end (20) is also provided with an aperture (21) of polygonal cross section in order to permit introduction of an instrument for fitting said neck (7) on the upper end (3) of the anchoring stem (1). This upper end (20) is continued in a co-linear manner by a portion (22) of greater diameter on which said male insert (6) rests.

Figure 15:
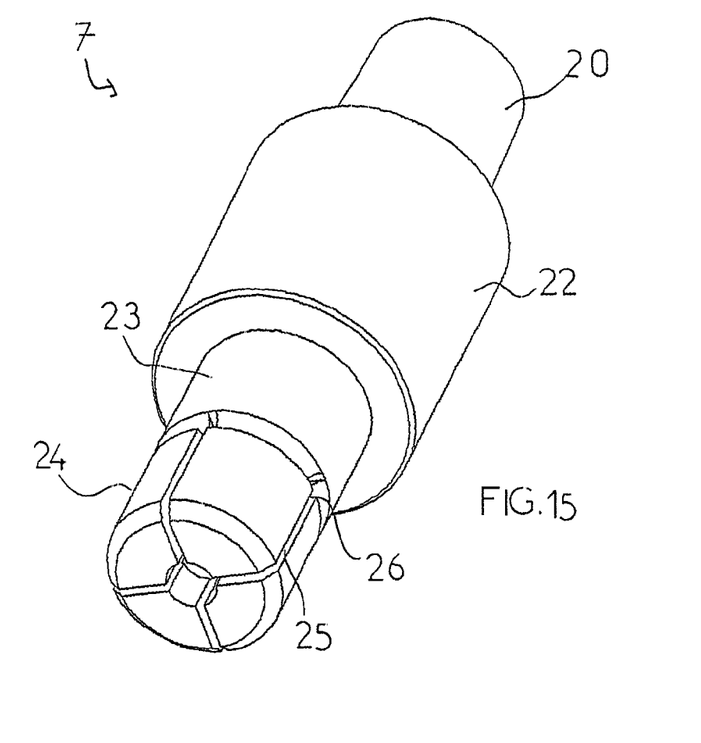
FIGS. 15 to 17 are diagrammatic perspective representations of the neck intended to cooperate with the stem of the implant according to the invention.
Figure 16:
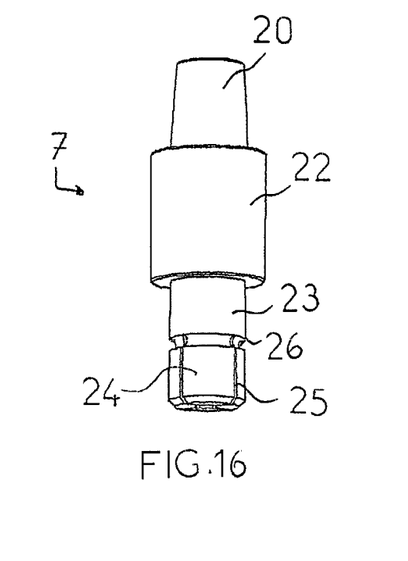
Figure 17:
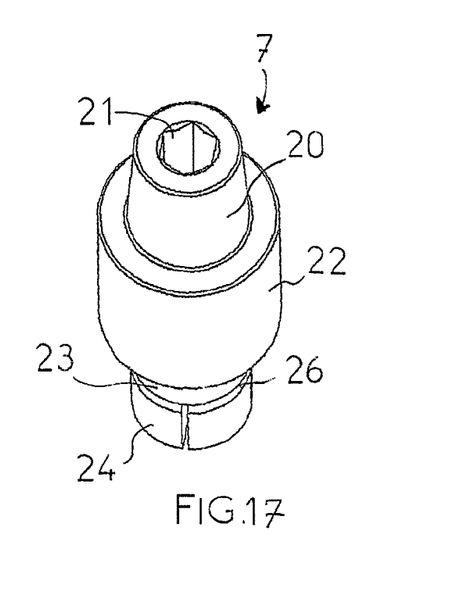

This portion (22) is in turn continued, again in a co-linear manner, by a cylindrical zone (23), then by a lower end (24) either in the from of a morse cone or a threading (25), these two zones being separated by a zone (26) of smaller cross section. This zone (26) is intended to give the lower end (24) a certain pliability.

The cylindrical zone (23) is intended to cooperate with the aperture (17) of the seat (13) of the basket (5) and in fact extends over a length corresponding substantially to the height of said seat and has a diameter corresponding, with slight clearance, to the internal diameter of said aperture.

The lower end (24) is for its part intended to cooperate with a recess (27) formed in the upper end (3) of the stem (1), or with a recess (28) formed in the intermediate element or short stem (8) in order to ensure fixation of said neck on these two respective elements, and fixation of the basket (5) and of the implant (6) on the anchoring stem (1). These recesses (27, 28) are in fact either provided with a shape able to cooperate with the morse cone shape of said lower end (24) or with an internal thread with a pitch corresponding to the threading (25) with which said lower end (24) is provided if appropriate.

In the case of the male insert, the basket (5) ensures stabilization of the stem and additionally promotes anchoring of the implant in the humerus.

The female insert, more particularly shown with reference to FIGS. 11 to 14, consists of a cup (30) in which a polyethylene insert (31) is clipped.

Figure 12:
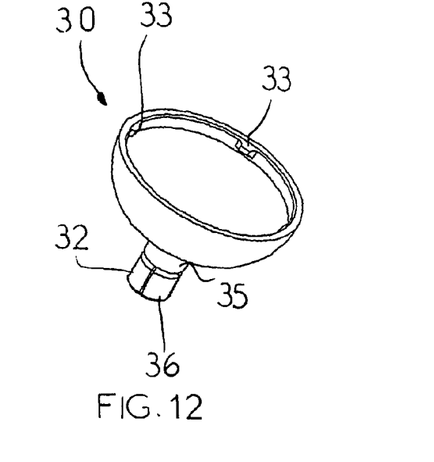
FIGS. 12 and 13 are diagrammatic perspective representations of the cup of the invention, in a top view and bottom view, respectively.
Figure 13:
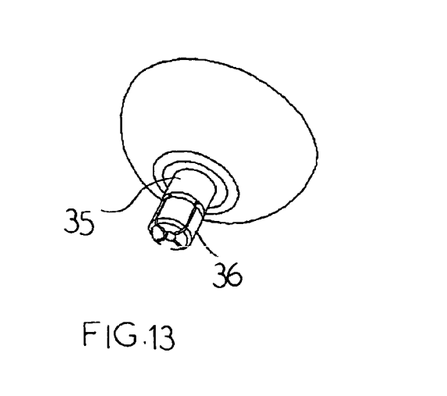

The cup (30), of substantially hemispherical shape, is continued by a shaft (32) starting from its lower pole, said shaft (32) fulfilling the same function as the aforementioned neck (7), and is thus provided like the latter:

with a cylindrical intermediate zone (35) intended to cooperate with the aperture (17) of the seat (13) of the basket (5), and with a lower zone (36) intended to cooperate with the recess (27) of the upper end (3) of the anchoring stem (1), or (28) of the intermediate element (8).

The outer envelope of the cup (30) corresponds substantially to the internal volume defined by the basket (5).

Figure 14:
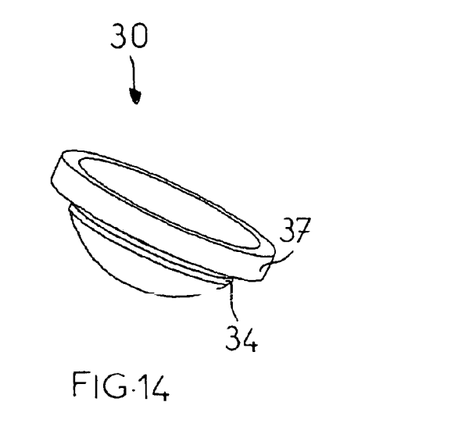
FIG. 14 is a diagrammatic perspective representation of the polyethylene insert which clips into the cup in FIGS. 12 and 13.

The polyethylene insert (31) clips into the cup (30). To do this, it is provided with annular ribs (34) which cooperate with studs (33) projecting in the direction of the volume defined by the cup and formed near the upper edge of said cup. The periphery of the insert (31) is additionally provided with a flange (37) intended to bear on the cup (30).

As will have been understood, the invention comprises two principal embodiments. One uses a long stem (1) intended to be inserted into the medullary canal of the humerus. The other uses a short stem (8) when implantation of a long stem is unnecessary. This short stem thus permits direct implantation of the humeral implant on the humerus.

As has already been stated, one of the advantages of this implant is that it requires limited resection of the spongy bone. The implant is put in place by means of cross-shaped instruments which match the shape of the basket-like support, which fact limits loss of bone.

Once in place, the male or female insert does not move, thanks to the close cooperation between the various elements.

The invention and the advantages which derive therefrom will be clear from the above description, and particular note will be made of the anatomical shape of the anchoring stem and of the adaptable properties of the implant.

The invention claimed is:

1. An adaptable humeral implant comprising:
   an anchoring stem with an upper end;
   a basket-shaped removable support formed having a circular seat with a through opening, the removable support comprising at least three spaced apart arc shaped branches giving the removable support a general hemispherical shape, the removable support being fixed at its pole to the upper end of the anchoring stem by means of an intermediate neck or shaft extending in the through opening of the removable support and being fixed to the upper end of the anchoring stem; and
   a male insert or a female insert adapted to cooperate with the glenoid cavity or a glenoid implant and also with the removable support, the male or female insert being fixed to the intermediate neck or shaft fixing the removable support to the upper end of the anchoring stem.

2. The adaptable humeral implant according to claim 1, wherein an outer face of the branches is provided with teeth which are intended to cooperate with spongy bone.

3. The adaptable humeral implant according to claim 1, wherein the circular seat of the basket shaped support has, on its lower face, radial sets of teeth which are spaced apart and are intended to permit correct positioning of the basket shaped support on the upper end of the anchoring stem.

4. The adaptable humeral implant according to claim 1, wherein the anchoring stem has, near its upper end, a recess of truncated cone shape, intended to cooperate with a lower end, also of truncated cone shape, of the intermediate neck or shaft.

5. The adaptable humeral implant according to claim 1, wherein the anchoring stem has, near its upper end, a recess of cylindrical shape, provided with an internal thread, intended to cooperate with a lower end of the intermediate neck or shaft provided with a corresponding threading.

6. The adaptable humeral implant according to claim 1, wherein the intermediate neck has three co-linear segments:
   an upper end in the form of a morse cone which is able to cooperate with the male insert;
   a portion of greater diameter on which said male insert rests;
   a cylindrical zone intended to cooperate with the through-opening of the seat of the basket shaped support, and continuing via a lower end which has either a morse cone shape or a threading, the cylindrical zone and the lower end being separated by a zone of smaller cross section.

7. The adaptable humeral implant according to claim 6, wherein the male insert or humeral prosthetic head is formed by a hemisphere whose base is provided with a conical recess, either centered or eccentric, able to cooperate with the upper end of the intermediate neck.

8. The adaptable humeral implant according to claim 1, wherein the female insert is formed by a cup whose outer envelope corresponds substantially to the internal volume defined by the basket shaped support, and which is continued via the intermediate shaft which is positioned at its pole, and which is provided with a cylindrical zone intended to cooperate with the through-opening of the seat of the basket shaped support, and continued via a lower end which is intended to cooperate with a recess at the upper end of the anchoring stem.

* * * * *